US008195305B2

(12) United States Patent
Nghiem et al.

(10) Patent No.: US 8,195,305 B2
(45) Date of Patent: Jun. 5, 2012

(54) IMPEDANCE-CONTROLLED IMPLANTABLE TELEMETRY ANTENNA

(75) Inventors: David Nghiem, Shoreview, MN (US); Ronald W. Solfest, Lino Lakes, MN (US); Mahesh Maddali, Mahtomedi, MN (US); Mark G. Deehr, Woodinville, WA (US); Dennis E. Larson, White Bear Lake Township, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 14 days.

(21) Appl. No.: 12/579,994

(22) Filed: Oct. 15, 2009

(65) Prior Publication Data

US 2010/0100157 A1 Apr. 22, 2010

Related U.S. Application Data

(60) Provisional application No. 61/106,068, filed on Oct. 16, 2008, provisional application No. 61/228,109, filed on Jul. 23, 2009.

(51) Int. Cl.
*A61N 1/00* (2006.01)
(52) U.S. Cl. ........................................ 607/60
(58) Field of Classification Search .................. 607/60; 343/700 MS, 791, 861, 873, 895; 455/193.1, 455/558
See application file for complete search history.

(56) References Cited

U.S. PATENT DOCUMENTS

| 6,809,701 | B2 | 10/2004 | Amundson et al. |
| 7,016,733 | B2 | 3/2006 | Dublin et al. |
| 7,317,946 | B2 | 1/2008 | Twetan et al. |
| 7,319,901 | B2 | 1/2008 | Dublin et al. |
| 7,467,014 | B2 | 12/2008 | Fuller et al. |
| 7,483,752 | B2 | 1/2009 | Von Arx et al. |
| 2005/0134520 | A1* | 6/2005 | Rawat et al. ............ 343/873 |
| 2006/0284770 | A1* | 12/2006 | Jo et al. ............ 343/700 MS |
| 2007/0288065 | A1 | 12/2007 | Christman et al. |
| 2007/0288066 | A1 | 12/2007 | Christman et al. |
| 2008/0303728 | A1 | 12/2008 | Lee et al. |
| 2008/0303743 | A1* | 12/2008 | Park et al. ............ 343/895 |
| 2010/0099959 | A1 | 4/2010 | Deehr et al. |
| 2010/0100157 | A1* | 4/2010 | Nghiem et al. ............ 607/60 |

OTHER PUBLICATIONS

Deehr, M. G., et al., "In-Header Perimeter RF Antenna", U.S. Appl. No. 12/579,980, filed Oct. 15, 2009, 31 pgs.

* cited by examiner

*Primary Examiner* — George Manuel
*Assistant Examiner* — Robert Wieland
(74) *Attorney, Agent, or Firm* — Schwegman, Lundberg & Woessner, P.A.

(57) ABSTRACT

A physical arrangement can be provided between at least a portion of a first segment of an implantable antenna with respect to a return conductor, and an input impedance of the implantable antenna can be controlled using the physical arrangement to provide a substantially conjugate match to an output impedance of an implantable telemetry circuit coupled to the implantable antenna.

28 Claims, 7 Drawing Sheets

IMPEDANCE-CONTROLLED IMPLANTABLE TELEMETRY ANTENNA

CROSS-REFERENCE TO RELATED APPLICATIONS

This application claims the benefit of U.S. Provisional Application No. 61/106,068, filed on Oct. 16, 2008 and U.S. Provisional Application No. 61/228,109, filed on Jul. 23, 2009 under 35 U.S.C. §119(e), which are hereby incorporated by reference in their entirety.

BACKGROUND

Medical devices can be implanted in a body to perform tasks including monitoring, detecting, or sensing physiological information in or otherwise associated with the body, diagnosing a physiological condition or disease, treating or providing a therapy for a physiological condition or disease, or restoring or otherwise altering the function of an organ or a tissue. An example of an implantable medical device can include a cardiac rhythm management device, such as a pacemaker, a cardiac resynchronization therapy device, a cardioverter or defibrillator, a neurological stimulator, a neuromuscular stimulator, a drug delivery system, or one or more other devices. In certain examples, the implantable medical device can include a telemetry circuit and an antenna, coupled to the telemetry circuit, the combination of which can be configured to provide wireless communication between the implantable medical device and an external device, such as to send information (e.g., physiological or other information) from the implantable medical device to the external device, or to receive information (e.g., programming instructions, operational parameters, or other information) at the implantable medical device from the external device.

Magnetic coupling can be used to provide short-range (e.g., a few centimeters) communication between an implantable medical device implanted in a body and an external device, or between an implantable medical device outside of the body and an external device. However, magnetic coupling communication largely relies on low frequency near-field radiation, where the field distribution is highly dependent upon the distance from, and orientation of, the antenna, which grossly limits the effective range of wireless communication between the implantable medical device and the external device.

As an alternative, low power radio frequency ("RF") communication can be used to provide communication between an implantable medical device and an external device having an extended range over magnetic coupling.

OVERVIEW

In an example, a physical arrangement can be provided between at least a portion of a first segment of an implantable antenna with respect to a return conductor, and an input impedance of the implantable antenna can be controlled using the physical arrangement to provide a substantially conjugate match to an output impedance of an implantable telemetry circuit coupled to the implantable antenna.

In Example 1, a system includes an implantable telemetry circuit having an output impedance, an implantable antenna electrically connected to the implantable telemetry circuit, the implantable antenna having a controllable input impedance and including a first segment, where the input impedance is controlled at least in part using a physical arrangement of at least a portion of the first segment with respect to a return conductor to provide a substantially conjugate match to the output impedance of the implantable telemetry circuit.

In Example 2, the return conductor of Example 1 optionally includes at least a portion of an implantable assembly housing.

In Example 3, the return conductor of any one or more of Examples 1-2 optionally includes at least a portion of a lead connection.

In Example 4, the input impedance of any one or more of Examples 1-3 is optionally controlled at least in part using a specified distance between the at least a portion of the first segment and the return conductor.

In Example 5, the input impedance of any one or more of Examples 1-4 is optionally controlled at least in part using an angle of the at least a portion of the first segment with respect to the return conductor.

In Example 6, the angle of at least a portion of the first segment of any one or more of Examples 1-5 is optionally configured to provide an incline of the at least a portion of the first segment with respect to the return conductor to increase an inductive portion of the input impedance.

In Example 7, the input impedance of any one or more of Examples 1-6 is optionally controlled at least in part using a shape of at least a portion of the first segment with respect to the return conductor.

In Example 8, the shape of the at least a portion of the first segment of any one or more of Examples 1-7 optionally includes a curve bending in more than one plane with respect to the return conductor.

In Example 9, the input impedance of any one or more of Examples 1-8 is optionally controlled at least in part using a specified length of the first segment.

In Example 10, the at least a portion of the specified length of the first segment of any one or more of Examples 1-9 optionally includes a transmission line, and the input impedance of any one or more of Examples 1-9 is optionally controlled at least in part using the transmission line.

In Example 11, the system of any one or more of Examples 1-10 optionally include a feedthrough configured to electrically connect the implantable antenna to the implantable telemetry circuit, wherein the specified length of the first segment is defined by a region specified from 5% of a length of the implantable antenna to 30% of the length of the implantable antenna as measured from the feedthrough.

In Example 12, the length of the implantable antenna of any one or more of Examples 1-11 is optionally a total path length of the implantable antenna.

In Example 13, the length of the implantable antenna of any one or more of Examples 1-12 is optionally an effective electrical length of the implantable antenna in a biological medium.

In Example 14, the length of the implantable antenna of any one or more of Examples 1-13 is optionally less than one quarter of a wavelength in free space in a specified operating frequency range.

In Example 15, the length of the implantable antenna of any one or more of Examples 1-14 is optionally less than one quarter of an effective wavelength in a biological medium in a specified operating frequency range.

In Example 16, the input impedance of any one or more of Examples 1-15 optionally includes an impedance realized looking out from a reference position, wherein the output impedance includes an impedance realized looking in from the reference position.

In Example 17, the reference position of any one or more of Examples 1-16 is optionally specified with respect to a feedthrough.

In Example 18, the implantable telemetry circuit of any one or more of Examples 1-17 optionally includes a matching circuit.

In Example 19, the system of any one or more of Examples 1-18 optionally includes a first medical device, wherein the implantable telemetry circuit and the implantable antenna are included as portions of the first medical device, and the system of any one or more of Examples 1-18 optionally includes a second medical device including a second implantable telemetry circuit having an output impedance substantially equal to the output impedance of the implantable telemetry circuit of the first medical device, and a second implantable antenna electrically connected to the second implantable telemetry circuit, the second implantable antenna having a second controllable input impedance and including a second segment, wherein the second input impedance is controlled at least in part using a second different physical arrangement of at least a portion of the second segment with respect to a second return conductor to provide a substantially conjugate match to the output impedance of the second implantable telemetry circuit.

In Example 20, the first medical device any one or more of Examples 1-19 optionally includes a first number of channels and the second medical device includes a second different number of channels.

In Example 21, a method includes providing a physical arrangement between at least a portion of a first segment of an implantable antenna of a first medical device with respect to a return conductor, and controlling an input impedance of the implantable antenna using the physical arrangement to provide a substantially conjugate match to an output impedance of an implantable telemetry circuit of the first medical device coupled to the implantable antenna.

In Example 22, the controlling the input impedance of the implantable antenna of Example 21 optionally includes using the physical arrangement of the at least a portion of the first segment with respect to an implantable assembly housing.

In Example 23, the controlling the input impedance of the implantable antenna of any one or more of Examples 21-22 optionally includes using the physical arrangement of the at least a portion of the first segment with respect to a lead connection.

In Example 24, the controlling the input impedance of the implantable antenna of any one or more of Examples 21-23 optionally includes using a specified distance between the at least a portion of the first segment and the return conductor.

In Example 25, the controlling the input impedance of the implantable antenna of any one or more of Examples 21-24 optionally includes using an angle of the at least a portion of the first segment with respect to the return conductor.

In Example 26, the using the angle of the at least a portion of the first segment with respect to the return conductor of any one or more of Examples 21-25 optionally includes using an incline of the at least a portion of the first segment with respect to the return conductor to increase an inductive portion of the input impedance.

In Example 27, the controlling the input impedance of the implantable antenna of any one or more of Examples 21-26 optionally includes using a shape of at least a portion of the first segment with respect to the return conductor.

In Example 28, the controlling the input impedance of the implantable antenna of any one or more of Examples 21-27 optionally includes using a specified length of the first segment.

In Example 29, at least a portion of the specified length of the first segment of any one or more of Examples 21-28 optionally includes a transmission line, and the controlling the input impedance of the implantable antenna of any one or more of Examples 21-28 optionally includes using the transmission line.

In Example 30, the using the specified length of the first segment of any one or more of Examples 21-29 optionally includes using a region specified from 5% of a length of the implantable antenna to 30% of the length of the implantable antenna as measured from a feedthrough.

In Example 31, the controlling the input impedance of the implantable antenna of any one or more of Examples 21-30 optionally includes controlling an impedance realized looking in from a reference position to provide a substantially conjugate match to the output impedance of the implantable telemetry circuit realized looking in from the reference position.

In Example 32, the controlling the input impedance of the implantable antenna of any one or more of Examples 21-31 optionally includes controlling an impedance realized looking in from a reference position specified with respect to a feedthrough.

In Example 33, the controlling the input impedance of the implantable antenna of any one or more of Examples 21-32 optionally includes using the physical arrangement to provide a substantially conjugate match to an output impedance of the implantable telemetry circuit and a matching circuit.

In Example 34, the method of any one or more of Examples 21-33 optionally includes providing a second different physical arrangement between at least a portion of a second segment of a second implantable antenna of a second medical device with respect to a second return conductor, controlling a second input impedance of the second implantable antenna using the second physical arrangement to provide a substantially conjugate match to an output impedance of a second implantable telemetry circuit of the second medical device coupled to the second implantable antenna, and wherein the output impedance of the second implantable telemetry circuit of the second medical device is substantially equal to the output impedance of the implantable telemetry circuit of the first medical device.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
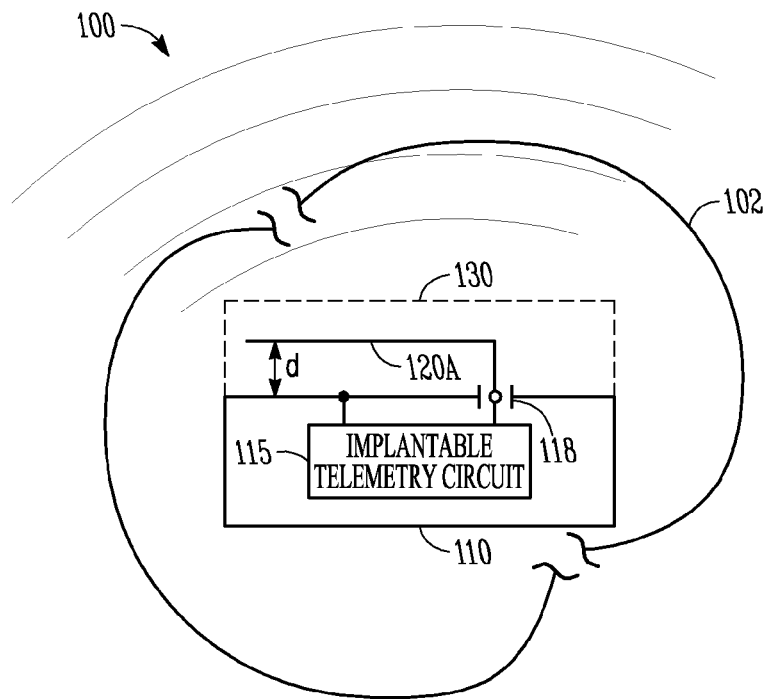
FIGS. 1A-1B illustrate generally examples of a system including an implantable antenna.

In an example, radio Frequency ("RF") power transfer between an implantable telemetry circuit and an implantable antenna can be maximized or enhanced by matching the complex conjugate of the impedance of the implantable antenna with the impedance of the implantable telemetry circuit. In certain examples, a matching circuit including one or more discrete components, integrated components, or one or more other components can be included as a portion, part, or component of the implantable telemetry circuit to provide the matching between the implantable telemetry circuit and the implantable antenna. The present inventors have recognized, among other things, that the matching circuit can be simplified or eliminated by controlling an input impedance of the implantable antenna. In an example, a telemetry circuit can include an RF transceiver module, and the implantable antenna can have an input impedance realizing a substantially conjugate match to an output impedance of the RF transceiver module without requiring a separate matching circuit. The present inventors have also recognized that the input impedance of the implantable antenna can be influenced by a physical arrangement of the implantable antenna with respect to one or more return conductors.

Further, the present inventors have recognized that a common design for one or more components of an implantable medical device (e.g., the implantable telemetry circuit, etc.) can be used across a product family while using one or more implantable antenna designs without requiring each product to include a different matching circuit. In an example, the product family can include a family of cardiac rhythm management ("CRM") devices, and two or more products included in the product family can include one or more of a single-channel CRM device, a dual-channel CRM device, a three-channel CRM device, or one or more other CRM devices. In this example, a channel can refer to an electrical lead connection (e.g., used for a therapy delivery, one or more diagnostic sensors, or for one or more other uses), or to one or more other connections. In this example, the one or more channels can be connected to one or more other circuits within an implantable assembly housing using one or more conductors. In this example, the two or more products can include an implantable antenna having a controllable input impedance. In an example, the input impedance can be controlled at least in part using a physical arrangement of at least a portion of the implantable antenna with respect to one or more return conductors. In this example, the controllable input impedance can be used to provide a substantially conjugate match to an output impedance of the implantable telemetry circuit (e.g., a common design implantable telemetry circuit for two or more products in the product family) included in two or more of the products in the product family, such as when a physical arrangement of the lead connections varies between two or more products, when spatial requirements permit the use of a longer implantable antenna, etc.

The present inventors have also recognized that the physical arrangement of the implantable antenna with respect to one or more conductors, such as lead connections, can influence the input impedance.

Figure 1B:
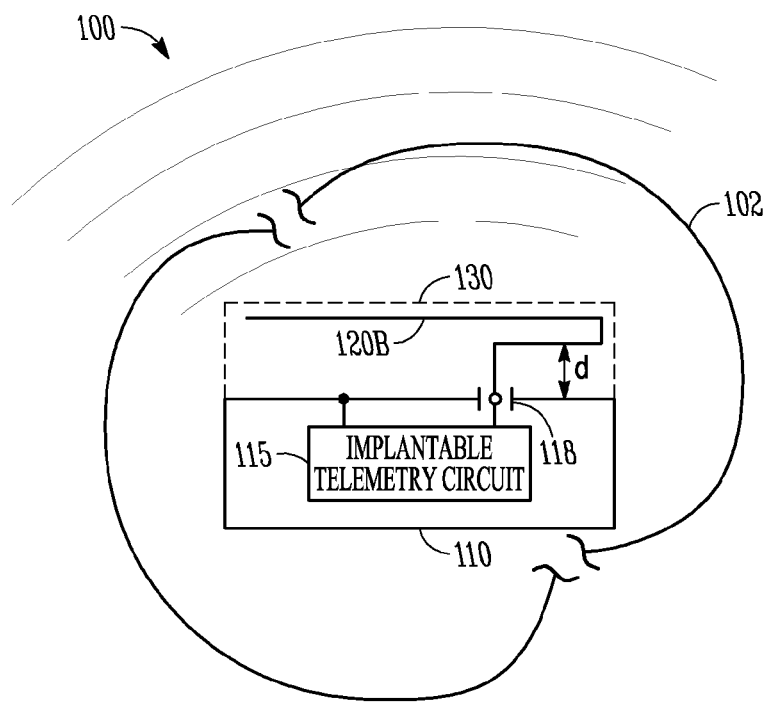

FIGS. 1A-1B illustrate generally examples of a system 100 including a first implantable antenna 120A having a first shape and a second implantable antenna 120B having a second shape. In an example, the first implantable antenna 120A or the second implantable antenna 120B can be electrically connected (e.g., using an electrical connection through a feedthrough 118, or using one or more other electrical connections) to an implantable telemetry circuit 115. In an example, the implantable telemetry circuit 115 can be electrically connected to a conductive portion of an implantable assembly housing 110. In certain examples, the implantable assembly housing 110 or one or more other conductive elements can be used as one or more return conductors to provide an RF energy return path to the implantable telemetry circuit 115. The present inventors have recognized, among other things, that an input impedance of the first implantable antenna 120A or the second implantable antenna 120B can be controlled at least in part using a physical arrangement of at least a portion of the first implantable antenna 120A or the second implantable antenna 120B with respect to the one or more return conductors. In certain examples, the shape of the first implantable antenna 120A or the second implantable antenna 120B, a distance ("d") between at least a portion of the first implantable antenna 120A or the second implantable antenna 120B and the one or more return conductors, or one or more other geometric or spatial parameters of the first implantable antenna 120A or the second implantable antenna 120B with respect to the one or more return conductors (e.g., at least a portion of the conductive portion of the implantable assembly housing 110) can be used to control the input impedance. In an example, as d is decreased, a capacitive coupling between the first implantable antenna 120A or the second implantable antenna 120B can be increased, and can increase a capacitive portion of the input impedance.

In certain examples, the implantable telemetry circuit 115 can provide an input or output port including one or more terminals, and the electrical connection to the first implantable antenna 120A or the second implantable antenna 120B can be made to a first terminal, and one or more return conductors can be electrically connected to one or more other terminals. In an example, one or more return conductors can be electrically connected to the implantable telemetry circuit 115 via a capacitive path formed by a discrete capacitor (e.g., an electromagnetic interference ("EMI") suppression capacitor, or one or more other discrete capacitors), one or more parasitic capacitors, or by one or more other capacitive paths. In an example, the electrical connection between the implantable telemetry circuit 115 and the first implantable antenna 120A or the second implantable antenna 120B can pass through the implantable assembly housing at the feedthrough 118. In certain examples, the feedthrough 118 can provide mechanical or electrical isolation between a region 130 exterior to the implantable assembly housing, or between the first implantable antenna 120A or the second implantable antenna 120B and a portion of the implantable assembly housing 110 (e.g., to prevent a short circuit when the portion of the implantable assembly housing 110 is conductive, or to provide one or more other types of isolation). In an example, the region 130 exterior to the housing can include a dielectric material to at least partially surround or support the first implantable antenna 120A or the second implantable antenna 120B, or to provide insulation from a surrounding medium 102, such as tissue or fluid.

Figure 2:
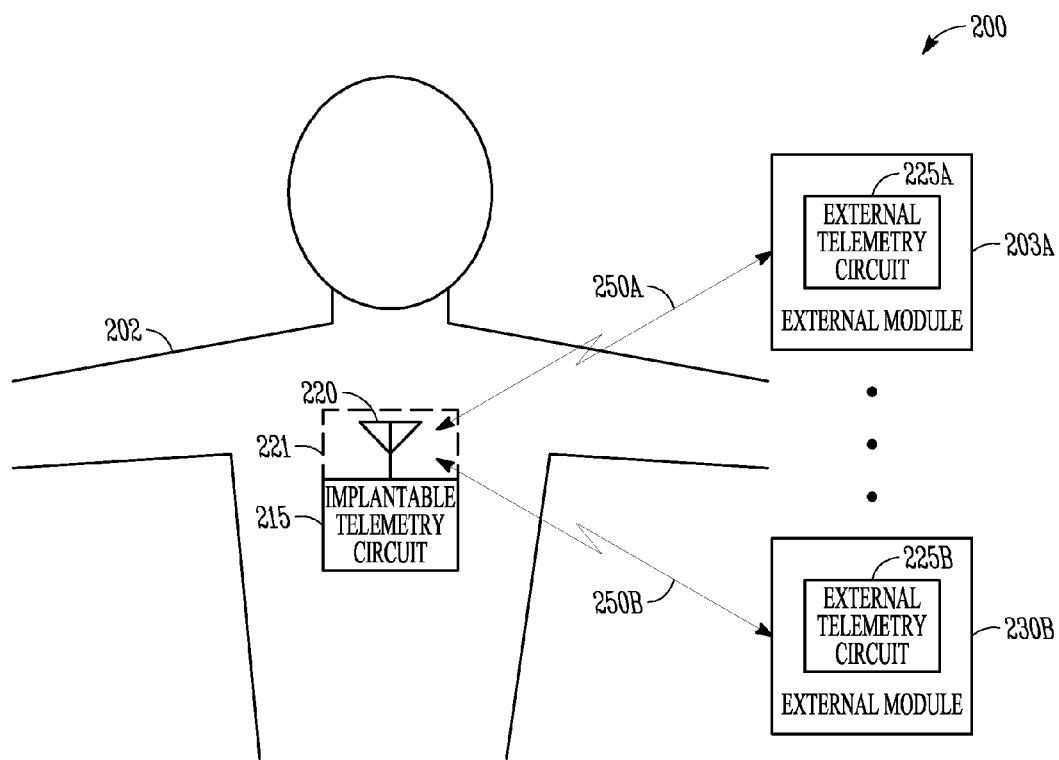
FIG. 2 illustrates generally an example a system including an implantable telemetry circuit and an implantable antenna in communication with one or more external modules.

FIG. 2 illustrates generally an example a system 200 including an implantable telemetry circuit 215 and an implantable antenna 220 in communication, such as in RF wireless communication (e.g., using a first RF wireless communication link 250A, a second RF wireless communication link 250B, etc.), with one or more external modules, such as a first external module 230A, a second external module 230B, etc. In an example, the implantable telemetry circuit 215 and the implantable antenna 220 can be implanted within a person (e.g., a patient 202), such as subcutaneously, intramuscularly, intrathoracically, or otherwise implanted within the patient 202. In an example, the implantable antenna 220 can be at least partially surrounded by a dielectric compartment 221 comprising a biocompatible dielectric material (e.g., the implantable antenna 220 can be inserted into a cavity within the compartment 221, or the compartment 221 can be formed at least in part by overmolding the antenna 220, or by one or more other techniques).

In an example, the first external module 230A or the second external module 230B can include an external telemetry circuit, such as a first external telemetry circuit 225A or a second external telemetry circuit 225B, respectively. In certain examples, the first RF wireless communication link 250A can be accomplished using a first range of RF operating frequencies, and the second RF wireless communication link 250B can be accomplished using a second range of RF operating frequencies different than the first range of operating frequencies. In other examples, the first external telemetry circuit 225A or the second external telemetry circuit 225B can use either a first or second operating range of frequencies, or both, for wireless communication. In certain examples, the first external telemetry circuit 225A or the second external telemetry circuit 225B can be electrically connected to one or more external antennas.

Figure 3:
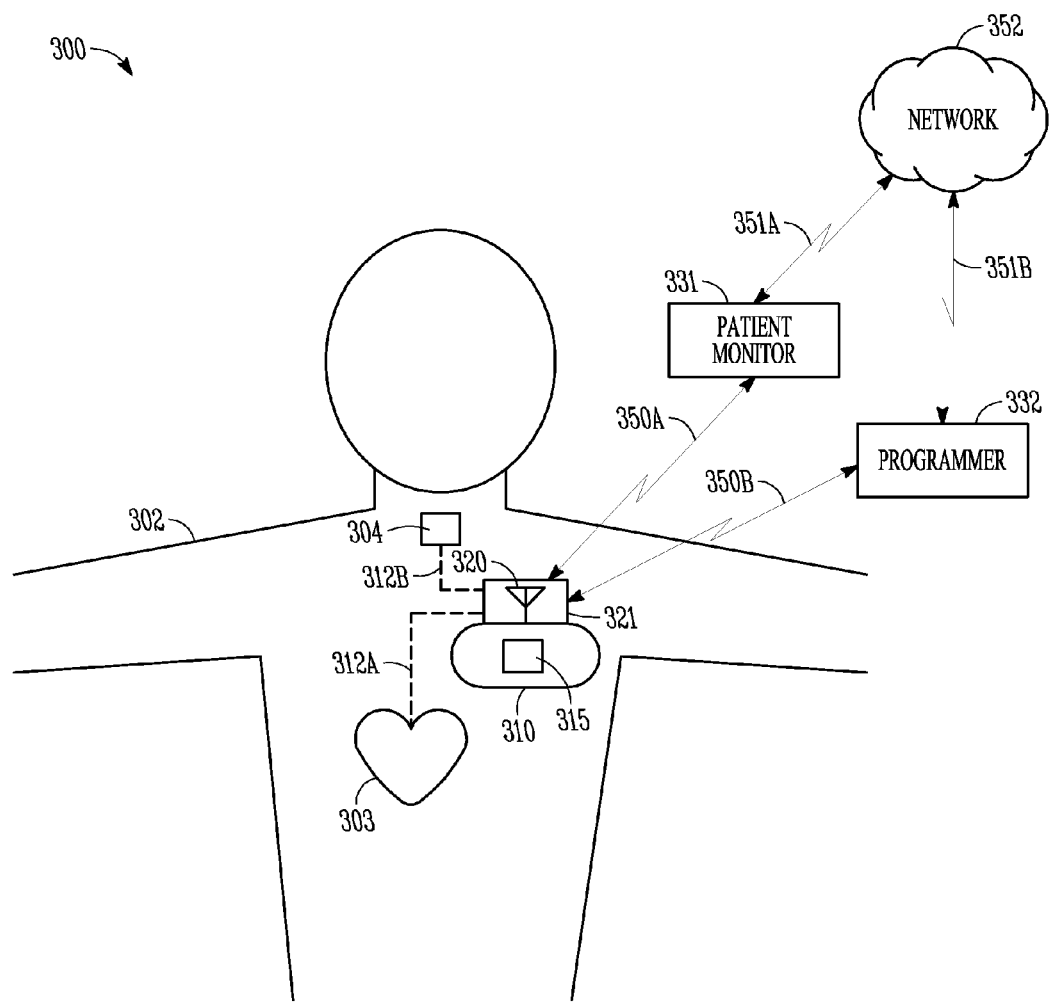
FIG. 3 illustrates generally an example of a system including an implantable medical device (IMD) in communication with at least one of a patient monitor or a programmer.

FIG. 3 illustrates generally an example of a system 300 including an implantable medical device ("IMD") 310, in communication, such as in RF wireless communication (e.g., using a first RF wireless communication link 350A, a second RF wireless communication link 350B, etc.), with at least one of a patient monitor 331 or a programmer 332. In an example, the IMD can be a cardiac rhythm management ("CRM") device, and can include one or more of cardiac resynchronization therapy circuitry, pacing circuitry, or tachyarrhythmia therapy circuitry (e.g., antitachyarrhythmic pacing or defibrillation shock).

In the example of FIG. 3, the IMD 310 can include a implantable telemetry circuit 315 electrically connected to an implantable antenna 320. As similarly discussed with respect to FIG. 2, in some examples, the first RF wireless communication link 350A or the second RF wireless communication link 350B can use more than one RF operating frequency range. In such examples, a single implantable antenna 320 can be configured to operate at two or more RF wireless operating frequencies to support the first RF wireless communication link 350A or the second RF wireless communication link 350B.

According to the example of FIG. 3, the implantable antenna 320 can be at least partially surrounded by a connector block 321 (e.g., generally referred to as a "header"). In certain examples, the connector block 321 can be at least partially made of a dielectric material. In various examples, the connector block 321 can also provide an electrical or mechanical connection between the IMD 310 and one or more implantable leads, such as a first implantable lead 312A or a second implantable lead 312B. In some examples, the first implantable lead 312A or the second implantable lead 312B can be routed within a patient body 302 to various sites, such as to provide a physiologic monitoring of an electrical or a mechanical signal, or to provide a therapy (e.g., an electrostimulus therapy, a targeted drug release, or other therapy). In the example of FIG. 3, the first implantable lead 312A can be routed to a cardiac tissue site 303 (e.g., an endocardial site, an epicardial site, a site within the myocardium, or other cardiac tissue site) to deliver a therapy, such as a cardiac rhythm management therapy, or the second implantable lead 312B can be routed to a neural target 304 (e.g., a vagal nerve or other neural target) to deliver a therapy, such as a neural stimulation therapy.

In certain examples, the patient monitor 331, the programmer 332, or both the patient monitor 331 and the programmer 332 can be communicatively coupled (e.g., using a first coupling 351A or a second coupling 351B) with a network 352. In an example, the first coupling 351A or the second coupling 351B can include a wired coupling or a wireless coupling. In an example, information can be wirelessly transferred from the IMD 310 to the patient monitor 331 or the programmer 332, and then transferred from the patient monitor 331 or the programmer 332 to the network 352 using the first coupling 351A or using the second coupling 351B.

Figure 4A:
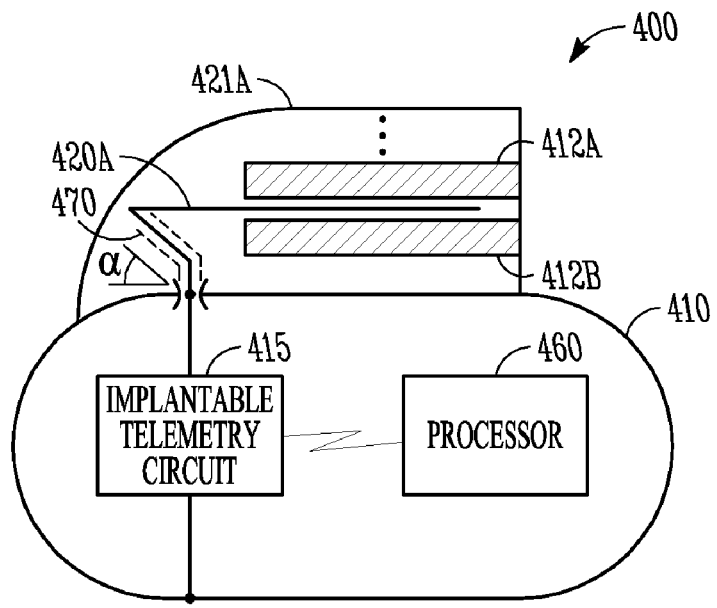
FIGS. 4A-4B illustrate generally examples of a system including an implantable antenna, an implantable telemetry circuit, and a processor.
Figure 4B:
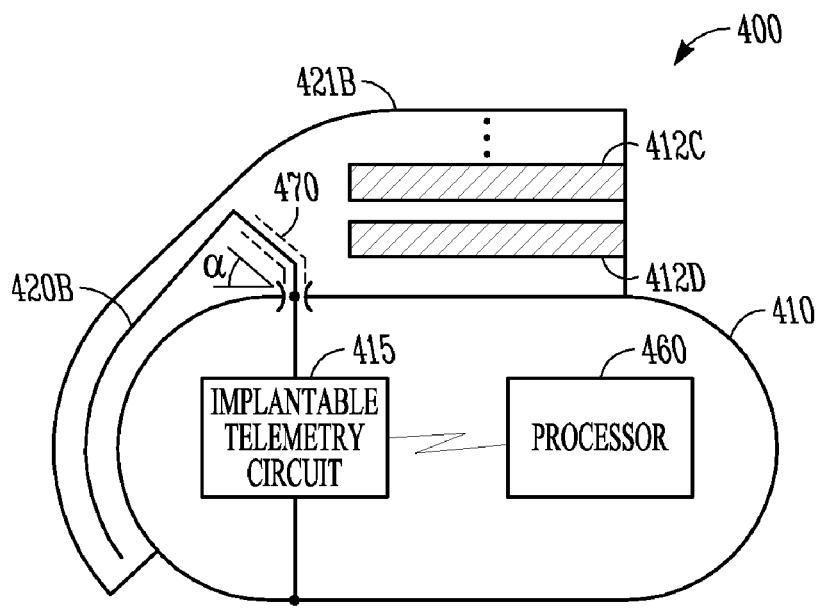

FIGS. 4A-4B illustrate generally examples of a system 400 including a first implantable antenna 420A, a second implantable antenna 420B, an implantable telemetry circuit 415, and a processor 460. In an example, the processor 460 can be communicatively coupled (e.g., using one or more of a wired connection, a wireless connection, or one or more other types of connections) to the implantable telemetry circuit 415 and configured to control of the implantable telemetry circuit 415, to provide information to be transmitted by the implantable telemetry circuit 415, to receive information from the implantable telemetry circuit 415, or to provide one or more other purposes or functions (e.g., therapy, diagnostic control, monitoring, etc.).

In an example, a first lead connector block 421A can at least partially surround or support the first implantable antenna 420A or one or more channel connections, such as a first lead electrical connection 412A, a second lead electrical connection 412B, etc. In an example, a second lead connector block 421B can at least partially surround or support the second implantable antenna 420B or one or more channel connections, such as a third lead electrical connection 412C, a fourth lead electrical connection 412D, etc. In certain examples, one or more additional lead electrical connections, one or more sensors, or one or more other conductive or non-conductive structures can be at least partially surrounded or supported by a first lead connector block 421A or a second lead connector block 421B. According to the example of FIG. 4B, the second lead connector block 421B can extend along an implantable assembly housing 410 to provide additional volume to at least partially surround or support the second implantable antenna 420B. As shown in the examples of FIGS. 4A-4B, the first implantable antenna 420A or the second implantable antenna 420B can be electrically coupled to the implantable telemetry circuit 415 through a feedthrough 418.

The present inventors have recognized, among other things, that at least a portion of a first segment of the first implantable antenna 420A or the second implantable antenna 420B can be used to at least in part control an input impedance of the first implantable antenna 420A or the second implantable antenna 420B.

The present inventors have also recognized, among other things, that decreasing a capacitive portion, increasing an inductive portion, or increasing a resistive portion of the input impedance of the first implantable antenna 420A or the second implantable antenna 420B can be used at least in part to provide a substantially conjugate match to the implantable telemetry circuit 415.

In an example, an angle ("α") of the first segment can be specified to control the impedance of the first implantable antenna 420A or the second implantable antenna 420B. In this example, the angle α can be adjusted to control one or more electrical characteristics (e.g., the inductive, resistive, or capacitive portions of the input impedance or one or more other characteristics) of the first implantable antenna 420A or the second implantable antenna 420B. In an example, a region of the first lead connector block 421A or the second lead connector block 421B can be used to provide a volume over which the angle α can be adjusted by controlling the physical arrangement of the portion of the first segment of the first implantable antenna 420A or the second implantable antenna 420B with respect to the implantable assembly housing 410. In an example, an otherwise unoccupied region in the first lead connector block 421A (e.g., implantable medical device header, or one or more other dielectric blocks), the second lead connector block 421B, or one or more other regions can provide the volume over which the angle α can be adjusted.

In an example, the angle α can be specified as an angle between the first segment and a top surface the implantable assembly housing 410. In this example, the top surface can be conductive, and can include one of one or more return conductors electrically connected to the implantable telemetry circuit 415. In an example, if the angle α is specified as 0°, the first segment can be parallel to the top surface of the implantable assembly housing 410. In other examples, if the angle α is specified as 90°, the first segment can be perpendicular to the top surface of the implantable assembly housing 410, and the capacitive portion of the input impedance of the first implantable antenna 420A or the second implantable antenna 420B can be reduced when compared to when the angle α is between 0° and <90°, or when the angle α is between >90° and 180°. In this example, the reduction in the capacitive portion can occur at least in part due to a reduced near-field capacitive coupling between the implantable assembly housing 410 the first implantable antenna 420A or the second implantable antenna 420B. In an example, the inductive portion of the input impedance of the first implantable antenna 420A or the second implantable antenna 420B can be increased when the angle α is adjusted. In this example, a capacitive portion of the input impedance of first implantable antenna 420A or the second implantable antenna 420B can become inductive as the angle α is increased (e.g., the first segment can form an incline with respect to the top surface of the implantable assembly housing 410), or as the total length is increased (e.g., a "break-over" behavior can occur where the input impedance transitions from capacitive to inductive as the angle α or the length is adjusted).

In an example, the resistive portion (e.g., a real resistance) of the first implantable telemetry antenna 420A can be increased as the angle α is increased, since a total length of the first implantable telemetry antenna 420A can be longer as the angle α becomes smaller (e.g., a length of the first segment can be adjusted as determined by the angle α without requiring movement or lengthening of a second segment of the implantable antenna 420A). In this example, the increase in the real resistance can be due at least in part to an increased ohmic loss of the increased total length of the first implantable telemetry antenna 420A. In an example, a real resistance of the second implantable telemetry antenna 420B can be decreased as the angle α is decreased, since the total length of the second implantable antenna 420B can be decreased as the angle α is decreased.

Figure 6A:
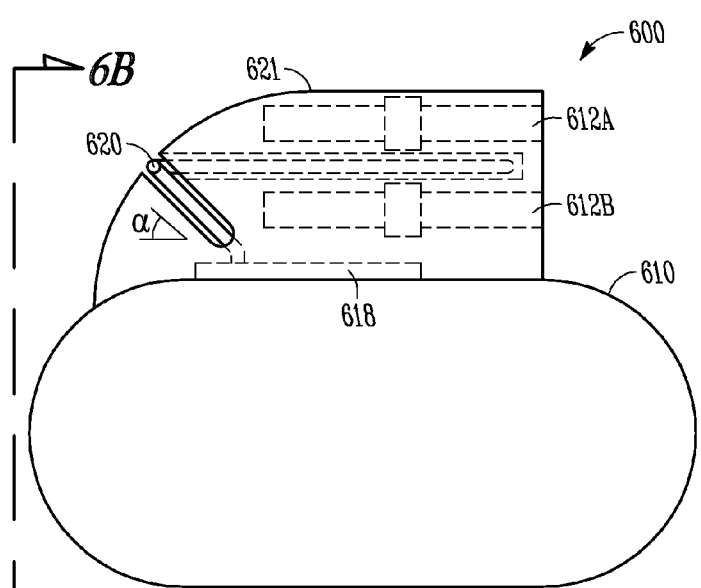
FIGS. 6A-6B illustrate generally an example of a system including an implantable antenna including a curve bending in more than one plane with respect to a return conductor.
Figure 6B:
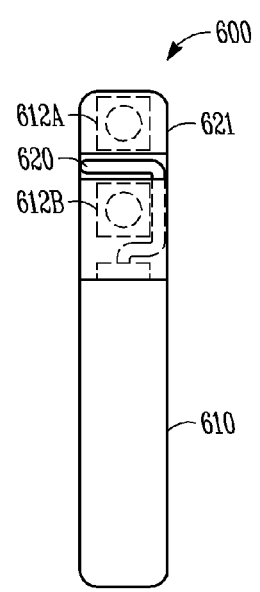

In certain examples, one or more transitions from one portion to another portion of the first implantable antenna 420A or the second implantable antenna 420B need not form sharp edges (e.g., a transition can be a smooth or continuous curve, spline, or one or more other curves, in one or more planes, such as illustrated in FIGS. 6A-6B).

In an example, the angle α, or the length of one or more portions of the first implantable antenna 420A or the second implantable antenna 420B can be adjusted, or a model or prototype of the first implantable antenna 420A or the second implantable antenna 420B can be simulated or constructed and tested on one or more implantable antennas including or lacking one or more impedance tuning portions (e.g., a specified volumetric region or cavity in the first lead connector block 421A or the second lead connector block 421B can be used to provide a region in which the input impedance can be adjusted during a design phase, a manufacturing phase, or at some other time).

In an example, at least a portion of the first segment of the first implantable antenna 420A or the second implantable antenna 420B can include a transmission line 470. In certain examples, the transmission line 470 can include a microstrip configuration, a coaxial configuration, a stripline configuration, a twin-axial configuration, or one or more other transmission line configurations supporting a transverse electromagnetic mode or a quasi-transverse electromagnetic mode. In these examples, a characteristic impedance of the transmission line 470 can be used, at least in part, to control the input impedance of the first implantable antenna 420A or the second implantable antenna 420B.

Figure 5:
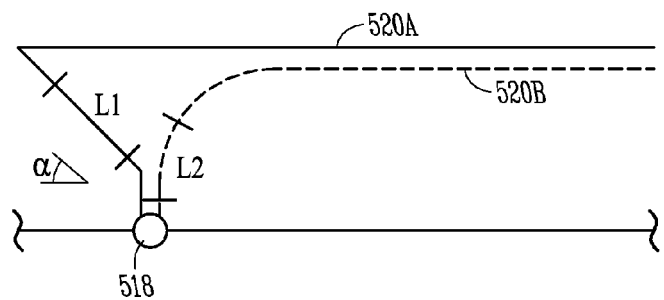
FIG. 5 illustrates generally examples of an effective electrical length of an implantable antenna.

FIG. 5 illustrates generally examples a path formed by an implantable antenna 520A and an effective electrical length 520B of an implantable antenna 520A. In an example, the input impedance of the implantable antenna 520A can be dominated by a region near the feedpoint 518 (e.g., a feedthrough 418 penetrating an implantable assembly housing 420A such as shown in the examples of FIGS. 4A-4B). The present inventors have recognized that the length or shape of the impedance dominating region can vary depending on the medium surrounding the implantable antenna 520A. In an example, when the implantable antenna 520A is surrounded by free space (e.g., air, or one or more other media having a relative dielectric constant of about 1.0), a segment length L1 can be specified along the implantable antenna 520A. In this example, the segment length L1 can range from 5% to 30% of the total path length of the implantable telemetry antenna 520A, and the effective electrical length of the implantable antenna 520A can be substantially the same as the total path length. In this example, in a region defined by the segment length L1, one or more shapes, or one or more angles (e.g., the angle α), can be used to controllably adjust the input impedance of the implantable antenna 520A (e.g., as in the examples of FIGS. 1A-1B, 4A-4B, 6, 8, 9 and 10). In other examples, the boundaries of the range of the segment length L1 can extend below 5% or above 30%. However, as the range is extended, the degree of control of the input impedance of the implantable antenna 520A can decrease.

In an example, when the implantable antenna 520A is surrounded by a biological medium (e.g., one or more of a bodily fluid, a skin tissue, a fat tissue, a muscle tissue, an organ tissue, a bone, or one or more other biological media), the implantable antenna 520A can have an effective electrical length 520B. In this example, a segment length L2 can range from 5% to 30% of the effective electrical length 520B of the implantable antenna 520A. In an example, the effective electrical length 520B of the implantable antenna 520A can be shorter than the total path length of the implantable antenna 520A, and the segment length L2 can be shorter than the segment length L1. In other examples, the boundaries of the range of the segment length L2 can extend below 5% or above 30%. However, as the range is extended, the degree of control of the input impedance of the effective electrical length 520B can decrease.

In certain examples, the total path length of the implantable antenna 520A, or an effective electrical length 520B can be less than one quarter of a wavelength. In certain examples, the wavelength can be a wavelength of an electromagnetic wave in free space, or an effective wavelength of an electromagnetic wave in a medium having a dielectric constant >1.0 (e.g., the biological medium, or one or more other media) in one or more specified operating frequency ranges. In certain examples, the region of the segment length L1, or the region of the segment length L2 can be used to controllably adjust an input impedance of one or more implantable antennas having one or more of an inverted-L configuration, an inverted-F configuration, a dipole configuration, a loop configuration, a monopole configuration, a patch configuration, a slot configuration, an array configuration, a fractal configuration, a planar configuration, a volumetric configuration, a serpentine configuration, or one or more other configurations.

FIGS. 6A-6B illustrate generally two views of an example of a system 600 including an implantable antenna 620 including a curve bending in more than one plane with respect to a return conductor, an implantable assembly housing 610, a lead connector block 621, a first lead connection 612A, a second lead connection 612B, and a feedthrough 618.

In an example, the lead connector block 621 can have a cavity, a void, a channel or one or more other regions to at least partially support or surround the implantable antenna 620. In the example shown in FIGS. 6A-6B, a portion of the implantable antenna 620 can be positioned on a side of the lead connector block 621. In certain examples, a portion of the implantable antenna 620 can be positioned above, around, between, encircling, or following one or more other paths around or near one or more lead connections (e.g., the first lead connection 612A, the second lead connection 612B, or one or more other electrical connections or features within the lead connector block 621).

In an example, the implantable antenna 620 can curve in more than one plane (e.g., a compound curve, spline, one or more other continuous curves, or a combination of piece-wise linear segments at one or more angles). In certain examples, an angle α, or one or more other angles can be specified with respect to one or more return conductors. In certain examples, the angle α, or the one or more other angles can be adjusted to control the input impedance of the implantable antenna 620. In certain examples, one or more additional lead connections can be added, or one or more of the first lead connection 612A, or the second lead connection 612B can be moved or removed, and the implantable antenna 620 can be substantially the same. In the examples of the adding, the removing, or the moving the one or more lead connections, the angle α, or the one or more other angles can be adjusted (e.g., during a design phase, or at one or more other times) to control the input impedance of the implantable antenna 620 to compensate for a change in coupling between the implantable antenna 620 and one or more return conductors (e.g., the implantable assembly housing, the one or more lead connections, or one or more other conductive structures) resulting at least in part from the adding, the moving or the removing of the lead connections. In the example shown in FIGS. 6A-6B, a region in the lead connector block 621 can be used to provide a volume over which the angle α can be "swept," or adjusted. In certain examples, the adjusting of the angle α, or the lengthening or shortening of a first segment of the implantable antenna 620 can use more than one plane or axis (e.g., one or more angles can be defined in one or more planes, and the one or more angles can be swept or adjusted).

Figure 7:
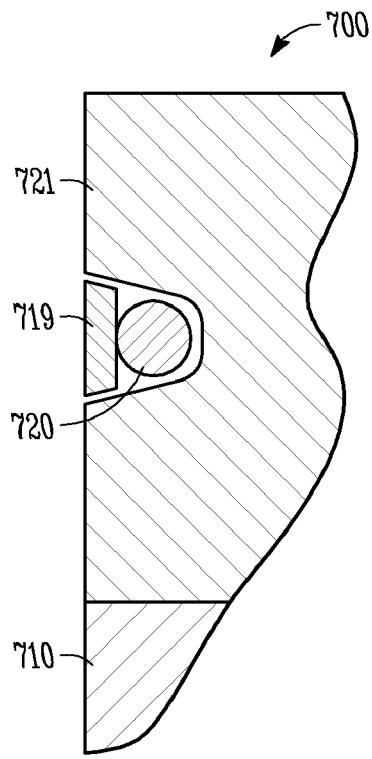
FIG. 7 illustrates generally an example of a section view of a system including an implantable antenna and a cover.

FIG. 7 illustrates generally an example of a section view of a system 700 including an implantable antenna 720 at least partially surrounded by a dielectric material 721 (e.g., a lead connector block, a radome, or one or more other dielectric materials), an implantable assembly housing 710, and a cover 719. In certain examples, the dielectric material 721 can be adhered, fastened, screwed, staked, molded or attached to the implantable assembly housing 710 using one or more mechanical attachments. In certain examples, the implantable antenna 720 can be a conductive wire, ribbon, tube, circuit trace on a substrate, or one or more other profiles or shapes. In an example, at least a portion of the implantable antenna 720 can be made from a biocompatible metal such as platinum-iridium, or one or more other metals or alloys. In an example, at least a portion of the implantable antenna 720 can be coated, enclosed, or surrounded in an insulating sheath, a jacket, a backfill material (e.g., a medical adhesive such as a silicone elastomer, or one or other adhesives or coatings) or one or more other insulating materials. In the example shown in FIG. 7, the implantable antenna 720 can be isolated mechanically or electrically from a medium surrounding the dielectric material 721 using a cover 719. In certain examples, the cover 719 is mechanically connected to one or more of the implantable antenna 720 or the dielectric material 721 using an adhesive, an interference fit, a fastener, or one or more other mechanical attachments. In an example, the cover 719 can be the same dielectric material as the dielectric block 721, or one or more other dielectric materials. In an example, the dielectric block 721 or the cover 719 can be a molded or a machined biocompatible thermoplastic polyurethane material (e.g., TECOTHANE™), or one or more other dielectric materials made using one or more other manufacturing techniques.

Figure 8:
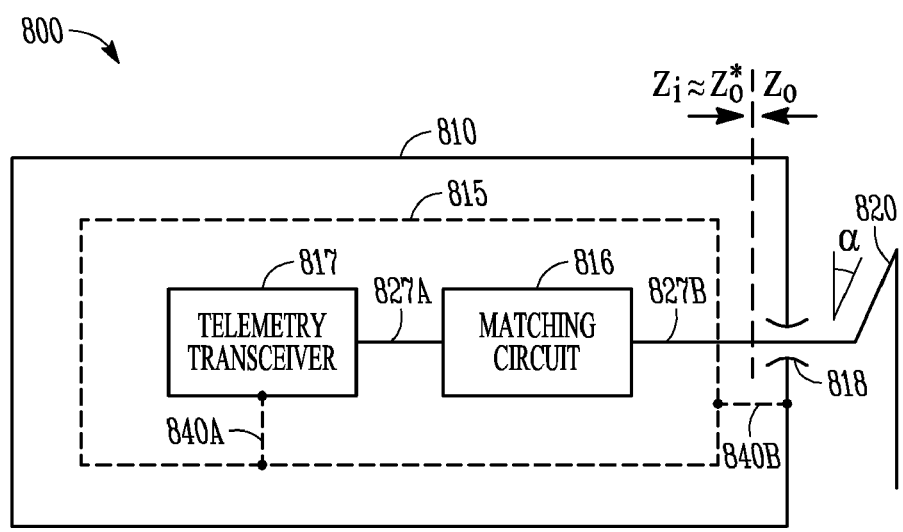
FIG. 8 illustrates generally an example of a system including a telemetry circuit coupled to an implantable antenna.

FIG. 8 illustrates generally an example of at least a portion of a system 800 including a telemetry circuit 815 electrically connected to an implantable antenna 820. In an example, the telemetry circuit 815 can include a telemetry transceiver ("XCVR") 817 coupled to a matching circuit 816 using a first RF input/output line 827A.

In an example, the telemetry circuit 815 can be partially or completely enclosed in an implantable assembly housing 810. In certain examples, the implantable assembly housing 810 can be made of a conductive material, such as a metal, a combination of metals, a biocompatible metal (e.g., titanium, platinum-iridium, or one or more other metals or alloys), etc. In an example, the telemetry transceiver 817 can be coupled to the telemetry circuit 815 using a first connection 840A. Further, the telemetry circuit 815 can be electrically connected to the implantable assembly housing 810 using a second connection 840B. In an example, an RF energy return path can be provided from the telemetry transceiver 817 to the telemetry circuit 815 using the first connection 840A, and from the telemetry circuit 815 to the implantable assembly housing 810 using the second connection 840B. In this example, the implantable assembly housing 810 can be used as a return conductor. In an example, one or more lead connections can be used as one or more return conductors.

In an example, the telemetry circuit 815 can be coupled to the implantable antenna 820 using a second RF input/output line 827B. In certain examples, the second RF input/output line 827B can penetrate the implantable assembly housing 810 to couple the telemetry circuit 815 and the implantable antenna 820. In other examples, at least a portion of the implantable antenna 820 or the telemetry circuit 815 can be contained in the implantable assembly housing 810, in a dielectric or other compartment coupled to the implantable assembly housing 810, or outside of the implantable assembly housing 810.

In an example, the implantable antenna 820 can have an angle, α=90°, resulting in an "L"-shaped implantable antenna 820 similar to the example shown in FIG. 1A. In this example, the implantable antenna 820 can provide a capacitive load to the telemetry circuit 815 (e.g., at the second RF input/output line 827B looking into the implantable antenna 820 through the feed-through 818). In certain examples, the matching circuit 816 (e.g., including an impedance matching element) can be included to compensate for an excess inductance or capacitance of the implantable antenna 820, or the telemetry transceiver 817. In the example of the angle α=90°, the impedance matching element 816 can include a discrete inductor. In the example of FIG. 8, the angle α<90° can reduce the value of or eliminate the need for the impedance matching element 816 within the telemetry circuit 815. In this example, an inductive portion can be increased or a capacitive portion can be decreased of an input impedance, $Z_i$, of the implantable antenna 820, looking in from a reference position as shown in FIG. 8.

In an example, the output impedance, $Z_o$, of the telemetry circuit can be 30−j60 Ohms looking in from a reference position as shown in FIG. 8. In this example, when the angle α=90°, the input impedance of the implantable antenna 820, $Z_i$, can be 10−j10 Ohms looking in from the reference position as shown in FIG. 8. In this example, the matching circuit 816 can provide a series resistance of 20 Ohms and a series inductance 50 Ohms (e.g., about 10 nanoHenries of inductance at a frequency of 800 MHz). In contrast, in a similar example, when the angle α<90°, the resistive portion of $Z_i$ can be increased, and the capacitive portion of $Z_i$ can be decreased. In certain examples, when the resistive portion of $Z_i$ can be increased, and the capacitive portion can be decreased, the size of the series resistance or series inductance of the matching circuit 816 can be reduced or eliminated.

In certain examples, a conjugate impedance match, $Z_i = Z_o^*$, between the first RF input/output line 827A and the implantable antenna 820, can provide or can enhance a power transfer to the implantable antenna 820 at a given frequency. In this example, a conjugate match can be described as when the real portion of $Z_i$=the real portion of $Z_o^*$ (e.g., Re$\{Z_i\}$=Re$\{Z_o^*\}$), and when the imaginary portion of $Z_i$ is equal to the magnitude of $Z_o$ and opposite in sign (e.g., Im$\{Z_i\}$=−Im$\{Z_o\}$).

In an example, when the imaginary part of $Z_i$ can be opposite in sign to the imaginary part of $Z_o$, the impedance matching element 816 can be omitted, or can be replaced with a purely resistive matching element (e.g., a substantially resistive mismatch can exist between the implantable antenna 820 and an output impedance of the telemetry transceiver 817).

In certain examples, a conjugate impedance match can be provided or otherwise configured between the telemetry circuit 815 and the implantable antenna 820, using, for example, the phase contribution of the first RF input/output line 827A and the second RF input/output line 827B, the impedance matching element 816 can provide an inductive contribution to the output impedance of the telemetry transceiver 817 to approximately cancel the capacitance of the implantable antenna 820.

In an example, the implantable antenna 820 can be operated at multiple frequencies, the matching element 816 can be used to provide an enhanced conjugate match at a first operating frequency range, and the impedance matching contribution from an angled portion of the implantable antenna 820 can be minimal in the first operating frequency range. Similarly, in an example, an impedance matching contribution from the matching element 816 can be minimal in a second operating frequency range, and the impedance matching contribution from an angled portion of the implantable antenna 820 can be used to provide an enhanced conjugate match (e.g., if the matching element 816 is operated at its unity-power factor self-resonant frequency, it can appear as a resistive element rather than as a capacitor or an inductor).

In an example, when the implantable antenna 820 is operated at multiple frequencies, the matching element 816 can be controllably switched out of the transmit and receive path between the first RF input/output line 819A and the second RF input/output line 819B. In certain examples, one or more values for the matching element 816 can be selected to provide an approximate conjugate match at more than one specified range of operating frequencies, or in more than one medium surrounding the implantable antenna 820.

In certain examples, the first or second operating frequency ranges can include one or more of a medical implant communication service (MICS) range from approximately 402 MHz to 405 MHz, a short range device (SRD) range from approximately 862 MHz to 870 MHz, a first industrial scientific and medical (ISM) range from approximately 902 MHz to 928 MHz, a second ISM range from approximately 2400 MHz to 2500 MHz, or one or more other operating frequency ranges.

In certain examples, the implantable telemetry circuit 815 can be configured as a transmitter, a receiver, or both. Generally, the principles described in connection with bi-directional wireless information transfer between an implantable antenna and another wireless device can also apply to unidirectional wireless information transfer. According to a physical principal of reciprocity, antenna behavior can be generally reciprocal (e.g., an antenna physically arranged as a transmitting antenna can also act as a receiving antenna having similar characteristics).

Figure 9:
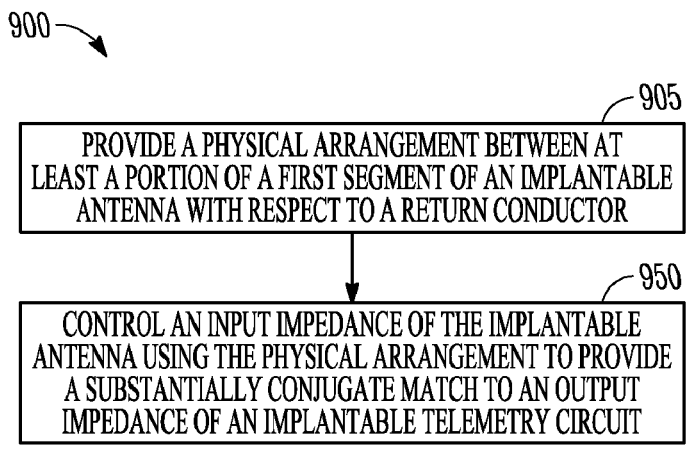
FIG. 9 illustrates generally an example of a method including controlling an input impedance of an implantable antenna.

FIG. 9 illustrates generally an example of a method 900 including at 910 controlling an input impedance of an implantable antenna (e.g., as in the examples of one or more of the systems of FIGS. 1A-1B, 2,3, 4A-4B, 5, 6A-6B, 7,8).

At 905, a physical arrangement between at least a portion of a first segment of an implantable antenna with respect to a return conductor can be provided. In an example, the using the physical arrangement of the first physical segment with respect to the one or more return conductors can use an implantable assembly housing (e.g., an implantable assembly housing 620 as shown in the examples of FIGS. 6A-6B) as one of the one or more return conductors.

At 910, an input impedance of the implantable antenna can be controlled using the physical arrangement to provide a substantially conjugate match to an output impedance of an implantable telemetry circuit. In an example, the using the physical arrangement of the first segment with respect to one or more return conductors to provide the substantially conjugate match to the output impedance of the implantable telemetry circuit (e.g., as in the examples of FIGS. 8, 10).

In an example, the using the physical arrangement of the at least a portion of the first segment with respect to the one or more return conductors can use one or more lead connections (e.g., a first lead connection 612A, or a second lead connection 612B as shown in the examples of FIGS. 6A-6B) as one or more of the one or more return conductors. In an example, the controlling the input impedance of the implantable antenna can include using a specified distance between the at least a portion of the first segment and the one or more return conductors (e.g., a distance "d" as shown in the examples of FIGS. 1A-1B).

In an example, the controlling the input impedance of the implantable antenna can include using an angle of the at least a portion of the first segment with respect to the one or more return conductors (e.g., an angle $\alpha$ as shown in FIGS. 1A-1B, 4A-4B, 5, 6A-6B, 8 with respect to the implantable assembly housing 620 as shown in the example of FIG. 6). In an example, the using the angle can include using an incline of the at least a portion of the first segment with respect to the return conductor to increase an inductive portion of the input impedance (e.g., as shown in the example of an implantable antenna 820 in FIG. 8).

In an example, the controlling the input impedance of the implantable antenna can include using one or more shapes of at least a portion of the first segment with respect to the one or more return conductors (e.g., as shown in the example of an implantable antenna 420 in FIG. 4). In an example, the controlling the input impedance of the implantable antenna can include using a specified length of the first segment (e.g., as shown in the context of the discussion of a length L1, and a length L2 in FIG. 5). In an example, the specified length of the first segment or a shape of the first segment with respect to the one or more return conductors can include using a region specified from 5% of a length of the implantable antenna to 30% of the length of the implantable antenna as measured from a feedthrough.

In an example, the controlling the input impedance of the implantable antenna can include controlling an impedance realized looking in from a reference position to provide a substantially conjugate match to the output impedance of the implantable telemetry circuit realized looking in from the reference position (e.g., as shown in the example of FIG. 8). In an example, the reference position can be specified with respect to a feedthrough. In an example, the controlling the input impedance of the implantable antenna can include using the physical arrangement to provide a substantially conjugate match to an output impedance of the combination of one or more of the implantable telemetry circuit and one or more matching circuits (e.g., as shown in the context of the discussion of FIG. 8).

Figure 10:
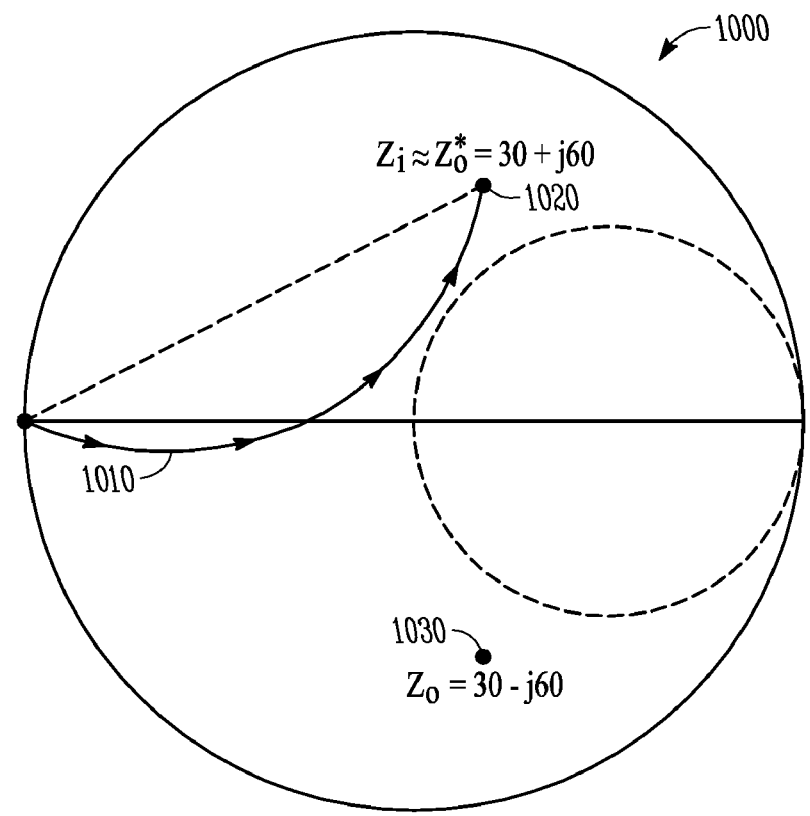
FIG. 10 illustrates generally an example of an impedance Smith Chart illustrating an example of an input impedance for an implantable antenna.

FIG. 10 illustrates generally an example of an impedance Smith Chart 1000 illustrating an example of an input impedance for an implantable antenna 1030, a conjugate match 1020, and a curve showing an implantable antenna input impedance 1010. In an example, a physical arrangement of a specified region of an implantable antenna can be controlled with respect to one or more return conductors (e.g., as shown in the examples of FIGS. 1A-1B, 2, 3, 4A-4B, 5, 6A-6B, 7-9).

In the example shown in FIG. 10, the output impedance 1030 can be $Z_o=30-j60$ Ohms, and the conjugate match impedance can be $Z_o^*=30+j60$ Ohms. In this example, one or more impedances can be normalized to 50 Ohms to be plotted on the impedance Smith Chart 1000. In this example, a normalized $Z_o=(30/50)-j(60/50)=0.4-j1.2$ ohms, and $Z_o^*=0.4+j1.2$ Ohms.

In an example, an angle of a first segment of an implantable antenna can be varied from 0° to an angle resulting in the conjugate match 1020. In this example, the input impedance 1010 can be short circuit when the angle is 0°, as shown on the Smith Chart 1000. In this example, as the angle is increased (e.g., an angle $\alpha$ as shown and in the examples of FIGS. 4A-4B, or one or more other angles), a capacitive portion of the input impedance 1010 can become inductive (e.g., a "break-over" as in the above discussion of the examples of FIGS. 4A-4B). In FIG. 10, the break-over can be shown as where the input impedance 1010 crosses the horizontal line. In this example, as the angle is further increased after the break-over, the inductive portion of the input impedance can become greater. In the example shown in FIG. 10, a resistive portion of the input impedance 1010 can become greater (e.g., as shown when the length of the implantable antenna increases or when the angle is increased as in the examples of FIGS. 1A-1B, 4A-4B, 5, 6A-6B, 7-9). In an example, the angle can specify an incline of the first segment of the implantable antenna with respect to an implantable assembly housing, and can be less <90° and >0° to provide the conjugate match.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim.

Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
an implantable telemetry circuit having an output impedance;
an implantable antenna electrically connected to the implantable telemetry circuit, the implantable antenna having a controllable input impedance and including a first segment located between the implantable telemetry circuit and the remainder of the antenna; and
a return conductor comprising a portion of an implantable assembly housing; and
wherein the input impedance is controlled at least in part using an angle of at least a portion of the first segment with respect to the return conductor, the portion including an incline with respect to the return conductor, and the portion configured to provide a substantially conjugate match to the output impedance of the implantable telemetry circuit.

2. The system of claim 1, wherein the return conductor comprises at least a portion of a lead connection.

3. The system of claim 1, wherein the input impedance is controlled at least in part using a specified distance between the at least a portion of the first segment including the incline, and the return conductor.

4. The system of claim 1, wherein the incline is configured to increase an inductive portion of the input impedance as compared to a first segment lacking an inclined portion.

5. The system of claim 1, wherein a shape of at least a portion of the first segment comprising the incline includes a curve bending in more than one plane with respect to the return conductor.

6. The system of claim 1, wherein the input impedance is controlled at least in part using a specified length of the first segment.

7. The system of claim 6, wherein at least a portion of the specified length of the first segment includes a transmission line; and
wherein the input impedance is controlled at least in part using the transmission line.

8. The system of claim 6, comprising:
a feedthrough configured to electrically connect the implantable antenna to the implantable telemetry circuit; and
wherein the specified length of the first segment is defined by a region specified from 5% of a length of the implantable antenna to 30% of the length of the implantable antenna as measured from the feedthrough.

9. The system of claim 8, wherein the length of the implantable antenna is a total path length of the implantable antenna.

10. The system of claim 8, wherein the length of the implantable antenna is an effective electrical length of the implantable antenna in a biological medium.

11. The system of claim 8, wherein the length of the implantable antenna is less than one quarter of a wavelength in free space in a specified operating frequency range.

12. The system of claim 8, wherein the length of the implantable antenna is less than one quarter of an effective wavelength in a biological medium in a specified operating frequency range.

13. The system of claim 1, wherein the input impedance includes an impedance realized looking out from a reference position; and
wherein the output impedance includes an impedance realized looking in from the reference position.

14. The system of claim 13, wherein the reference position is specified with respect to a feedthrough.

15. The system of claim 1, wherein the implantable telemetry circuit includes a matching circuit.

16. The system of claim 1, including:
a first medical device, wherein the implantable telemetry circuit and the implantable antenna are included as portions of the first medical device; and
a second medical device, including:
a second implantable telemetry circuit having an output impedance substantially equal to the output impedance of the implantable telemetry circuit of the first medical device;
a second implantable antenna electrically connected to the second implantable telemetry circuit, the second implantable antenna having a second controllable input impedance and including a second segment; and
wherein the second input impedance is controlled at least in part using a second different physical arrangement of at least a portion of the second segment with respect to a second return conductor to provide a substantially conjugate match to the output impedance of the second implantable telemetry circuit.

17. The system of claim 16, wherein the first medical device includes a first number of channels and the second medical device includes a second different number of channels.

18. A method comprising:
providing an angle of at least a portion of a first segment of an implantable antenna of a first medical device with respect to a return conductor, the portion including an incline with respect to the return conductor; and
controlling an input impedance of the implantable antenna using the portion of the first segment provide a substantially conjugate match to an output impedance of an implantable telemetry circuit of the first medical device coupled to the implantable antenna;
wherein the return conductor comprises a portion of an implantable assembly housing; and
wherein the first segment is located between the implantable telemetry circuit and the remainder of the antenna.

19. The method of claim 18, wherein the controlling the input impedance of the implantable antenna includes using the physical arrangement of at least a portion of the first segment with respect to a lead connection.

20. The method of claim 18, wherein the controlling the input impedance of the implantable antenna includes using a specified distance between at least a portion of the first segment including the incline, and the return conductor.

21. The method of claim 18, comprising using the angle of at least a portion of the first segment with respect to the return conductor to increase an inductive portion of the input impedance as compared to a first segment lacking an inclined portion.

22. The method of claim 18, wherein the controlling the input impedance of the implantable antenna includes using a specified length of the first segment.

23. The method of claim 22, wherein at least a portion of the specified length of the first segment includes a transmission line; and wherein the controlling the input impedance of the implantable antenna includes using the transmission line.

24. The method of claim 22, wherein the using the specified length of the first segment includes using a region specified from 5% of a length of the implantable antenna to 30% of the length of the implantable antenna as measured from a feedthrough.

25. The method of claim 18, wherein the controlling the input impedance of the implantable antenna includes controlling an impedance realized looking in from a reference position to provide a substantially conjugate match to the output impedance of the implantable telemetry circuit realized looking in from the reference position.

26. The method of claim 25, wherein the controlling the input impedance of the implantable antenna includes controlling an impedance realized looking in from a reference position specified with respect to a feedthrough.

27. The method of claim 18, wherein the controlling the input impedance of the implantable antenna includes using the physical arrangement to provide a substantially conjugate match to an output impedance of the implantable telemetry circuit and a matching circuit.

28. The method of claim 18, including:
providing a second different physical arrangement between at least a portion of a second segment of a second implantable antenna of a second medical device with respect to a second return conductor;
controlling a second input impedance of the second implantable antenna using the second physical arrangement to provide a substantially conjugate match to an output impedance of a second implantable telemetry circuit of the second medical device coupled to the second implantable antenna; and
wherein the output impedance of the second implantable telemetry circuit of the second medical device is substantially equal to the output impedance of the implantable telemetry circuit of the first medical device.

* * * * *